(12) United States Patent
Buhlmann et al.

(10) Patent No.: US 9,008,791 B2
(45) Date of Patent: Apr. 14, 2015

(54) ELECTRODE SYSTEM FOR TRANSCUTANEOUS NERVE AND/OR MUSCLE STIMULATION

(75) Inventors: Félix Buhlmann, Lausanne (CH); Klaus Schönenberger, Mex (CH); Pierre Rigaux, Verlaine (BE)

(73) Assignee: DJO Global Switzerland Sàrl, Ecublens (FR)

( * ) Notice: Subject to any disclaimer, the term of this patent is extended or adjusted under 35 U.S.C. 154(b) by 1741 days.

(21) Appl. No.: 11/792,635

(22) PCT Filed: Dec. 9, 2005

(86) PCT No.: PCT/IB2005/054156
§ 371 (c)(1),
(2), (4) Date: Aug. 20, 2008

(87) PCT Pub. No.: WO2006/061805
PCT Pub. Date: Jun. 15, 2006

(65) Prior Publication Data
US 2009/0118789 A1   May 7, 2009

(30) Foreign Application Priority Data

Dec. 9, 2004  (CH) ..................................... 2044/04

(51) Int. Cl.
*A61N 1/00* (2006.01)
*A61N 1/04* (2006.01)
(Continued)

(52) U.S. Cl.
CPC .............. *A61N 1/046* (2013.01); *A61N 1/0452* (2013.01); *A61N 1/0456* (2013.01); *A61N 1/36021* (2013.01); *A61N 1/3625* (2013.01); *A61N 1/39* (2013.01)

(58) Field of Classification Search
CPC ..... A61N 1/0452; A61N 1/0456; A61N 1/18; A61N 1/36014; A61N 1/36021
USPC ................................. 607/46, 47, 63
See application file for complete search history.

(56) References Cited

U.S. PATENT DOCUMENTS 5,052,391 A   10/1991   Silberstone et al.
5,058,605 A *  10/1991   Slovak ............................ 607/72
(Continued)

FOREIGN PATENT DOCUMENTS

EP   0 830 875   3/1998

OTHER PUBLICATIONS

Recorded Assignment Executed by Félix Buhlmann and Klaus Schönenberger (2 pages).
(Continued)

*Primary Examiner* — Scott Getzow
(74) *Attorney, Agent, or Firm* — Knobbe, Martens, Olson & Bear, LLP

(57) ABSTRACT

An electrode system for transcutaneous nerve and/or muscle stimulation that includes a pair of stimulating electrodes and a stimulation current generator for generating a nerve and/or muscle stimulation current between the stimulating electrodes. The system also includes a current-injecting electrode arranged in proximity to one of the stimulating electrodes, and an injection-current generator located in the area of the current-injecting electrode. The current-injecting electrode and the corresponding injection-current generator reduce, or even eliminate, undesirable sensations resulting from an excitation of subcutaneous receptors by the stimulation current.

14 Claims, 2 Drawing Sheets

(51) Int. Cl.
   *A61N 1/36*   (2006.01)
   *A61N 1/362*  (2006.01)
   *A61N 1/39*   (2006.01)

(56) References Cited

U.S. PATENT DOCUMENTS

| | | | | |
|---|---|---|---|---|
| 5,282,843 | A * | 2/1994 | Freeman | 607/115 |
| 5,314,459 | A * | 5/1994 | Swanson et al. | 607/122 |
| 6,341,237 | B1 | 1/2002 | Hurtado | |
| 6,438,418 | B1 | 8/2002 | Swerdlow et al. | |
| 6,567,697 | B1 * | 5/2003 | Kroll et al. | 607/5 |
| 6,697,670 | B2 * | 2/2004 | Chomenky et al. | 607/2 |
| 6,711,442 | B1 * | 3/2004 | Swerdlow et al. | 607/63 |
| 2006/0122649 | A1 * | 6/2006 | Ghanem et al. | 607/9 |

OTHER PUBLICATIONS

Recorded Assignment Executed by Félix Buhlmann, Klaus Schönenberger, and Pierre Rigaux, as Annotated by Pierre Rigaux (4 pages).
Combined Declaration and Power of Attorney Executed by Félix Buhlmann and Klaus Schönenberger (3 pages).
Combined Declaration and Power of Attorney for Patent Application Executed by Félix Buhlmann, Klaus Schönenberger, and Pierre Rigaux, as Annotated by Pierre Rigaux (5 pages).
Certified Translation of Pierre Rigaux's Annotations (4 pages).
Statement Executed by Félix Buhlmann, Stating that Klaus Schönenberger is a joint inventor of the present invention (1 page) dated Jul. 18, 2008.

* cited by examiner

ELECTRODE SYSTEM FOR TRANSCUTANEOUS NERVE AND/OR MUSCLE STIMULATION

RELATED APPLICATIONS

This application claims priority to PCT Application No. PCT/IB2005/054156 filed Dec. 9, 2005, and Switzerland Application No. CH02044/04 filed Dec. 9, 2004, the disclosures of which are hereby incorporated by reference in their entirety.

FIELD OF THE INVENTION

The present invention relates to the transcutaneous electrical stimulation of nerves and muscles by means of a system that comprises a pair of electrodes connected to a current generator.

This type of stimulation can be used in a large number of fields. Examples that may be mentioned include the fields of neuromuscular electrostimulation for sport or medical purposes, anesthesia, defibrillation, or regulation of heart beat by means of an external pacemaker.

BACKGROUND

For transcutaneous nerve and/or muscle stimulation, it is known to generate a current between two electrodes placed on the skin. By way of an illustrative example, the application EP 1 095 670, incorporated by reference in the present application, describes such an electrical neuromuscular stimulator that uses stimulating electrodes and a generator of electrical impulses.

In addition to stimulating the nerves and/or muscles, the current also stimulates the subcutaneous receptors that are situated between the skin surface and the nerves and/or muscles that are to be stimulated.

However, the subcutaneous receptors are sensitive to various factors, such as temperature, pressure or pain. Consequently, their excitation by an electrical current may induce undesirable effects as far as the user is concerned, for example pain, stinging sensation, etc.

There is therefore a need to be able to reduce, or even completely eliminate, the undesirable sensations that are experienced during transcutaneous nerve and/or muscle stimulation by electrodes.

SUMMARY OF THE INVENTION

It is therefore an object of the invention to improve the systems known from the prior art.

More particularly, it is an object of the invention to make available a system for transcutaneous electrical stimulation of nerves and muscles that overcomes the aforementioned problem of the occurrence of undesirable sensations during the stimulation.

It is another object of the invention to make available a simple device that is easy to use and that is effective and provides improved comfort for the user.

To this end, the invention relates to an electrode system for transcutaneous nerve and/or muscle stimulation, comprising at least: a pair of stimulating electrodes, stimulating means for generating a nerve and/or muscle stimulation current between said stimulating electrodes, said system further comprising a current-injecting electrode arranged in proximity to one of the stimulating electrodes, current-generating means in the area of said injecting electrode, between said injecting electrode and the nearest stimulating electrode, in such a way as to reduce, or even eliminate, the undesirable sensations possibly resulting from the excitation of the subcutaneous receptors by said stimulation current.

For the purposes of this application, proximity means, a distance that is shorter than the distance between the stimulating electrodes.

Thus, according to the invention, the system comprises two circuits, one for stimulating the muscles and/or nerves, and the other for making the subcutaneous receptors less excitable, thereby improving user comfort. This specific action on the subcutaneous receptors is made possible by the presence of electrodes that are located near one another, such that the injected current does not extend depthwise but instead remains at the surface. Moreover, the forms of injected current are chosen in such a way as to achieve this object.

The current-injecting electrode is advantageously arranged around the stimulating electrode.

According to a particular embodiment of the invention, each stimulating electrode is surrounded by a current-injecting electrode.

According to another particular embodiment, the stimulating electrode comprises a first part surrounded by a first part of the current-injecting electrode, itself being surrounded by a second part of the stimulating electrode, which is itself surrounded by a second part of the current-injecting electrode. This configuration can repeat itself several times.

The invention also relates to a method of use of the aforementioned electrode system, said method being characterized in that a form of current generated by the current-generating means in the area of said injecting electrode is chosen in such a way as to reduce, or even eliminate, the undesirable sensations possibly resulting from the excitation of the subcutaneous receptors by said stimulation current.

A first way of achieving this object is to choose an injection current strength in such a way as to reduce or to annul the total current circulating in the area of the subcutaneous receptors. In this case, the injected current, which is directed toward the corresponding stimulating electrode, compensates for the stimulation current emerging from the stimulating electrode.

It will be noted here that the compensation between stimulation current and injected current results in annulment of the total current exclusively in the area of the subcutaneous receptors. Such annulment of the current is not produced in the area of the nerves and/or muscles that are to be stimulated.

A second way of proceeding is to choose a form of injection current in such a way as to induce a blockage of the nerve transmission to the subcutaneous receptors. This provides an anesthetizing effect on the subcutaneous receptors.

A third approach is to excite the area surrounding the subcutaneous receptors (TENS effect), without inducing pain. In this case, the pain signal sent by the receptors to the brain is embedded in a general signal. Typically, in the TENS effect, a permanent tingling sensation is experienced by the user, said tingling sensation masking other sensations such as pain. In this way, one sensation is covered by another.

Another approach is to first send a local current, which renders the subcutaneous receptors less excitable, and then to send the stimulation current.

Different currents can be used at staggered intervals.

According to one variant, the receptors are charged, and they will be less sensitive to the stimulation current.

Typically, the principles set out in the publications WO 02/065896 or US 2004/0127953 can be applied for the forms of current generated in the system according to the invention, these publications being incorporated by reference in the present application in respect of the signals that can be used. Other examples are given in the following publications:

Bhadra N, Kilgore K L, "Direct current electrical conduction block of peripheral nerve", IEEE Trans Neural Syst Rehabil Eng. 2004 September; 12(3): 313-324;

Kilgore K L, Bhadra N, "Nerve conduction block utilising high-frequency alternating current", Med Biol Eng Comput. 2004 May; 42(3): 394-406;

Bhadra N, Kilgore K L, Creasey G H, "Block of Mammalian Motor Nerve Conduction Using High Frequency Alternating Current", 10th Annual Conference of the International FES Society, July 2005, Montreal, Canada;

Kilgore K L, Bhadra N, "Block of Nerve Conduction Using High Frequency Alternating Current", 9th Annual Conference of the International FES Society, September 2004, Bournemouth, UK.

These documents provide explanations of the various methods for obtaining a conduction block (collision block, hyperpolarization, depolarization, high-frequency AC block).

As has been indicated above, it is also possible to use current forms that either mask the sensations of pain (TENS) or reduce the current density or the electrical charge density in the area of the sensitive fibers of the skin. Of course, this list is not exhaustive, and other forms may be envisioned, the idea being to send an injection current to the subcutaneous receptors in order to make them less excitable.

BRIEF DESCRIPTION OF THE FIGURES

The invention will be better understood from the following detailed description of two embodiments thereof. To this end, a non-limiting example is shown schematically in the following figures, in which.

DETAILED DESCRIPTION

Figure 1:
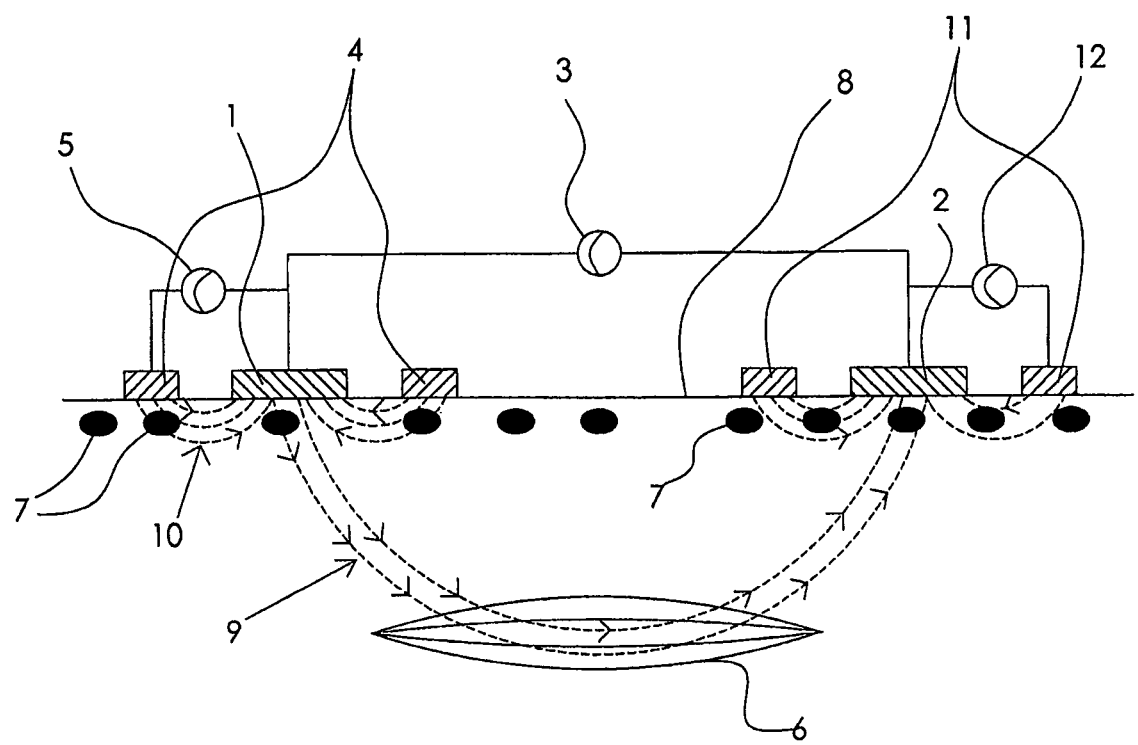
FIG. 1 illustrates a cross section of the system according to the invention placed on the skin.
Figure 2:
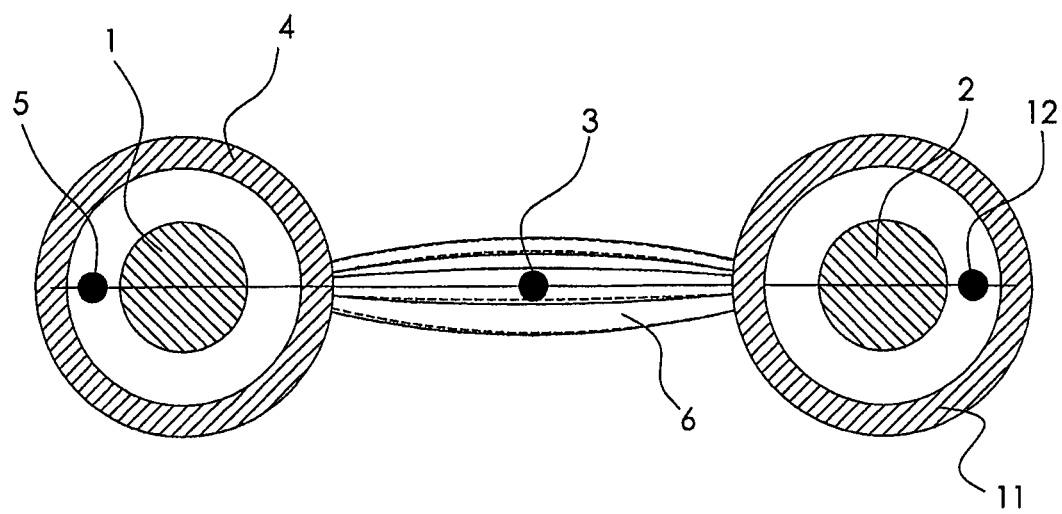
FIG. 2 shows a plan view of the system from FIG. 1.

The system according to the first embodiment illustrated in FIGS. 1 and 2 comprises two stimulating electrodes 1 and 2 that are connected to a stimulation current generator 3. Beneath the skin 8, a stimulation current 9 moves between the stimulating electrodes 1 and 2 and stimulates a muscle 6.

Each stimulating electrode 1 and 2 is surrounded by a current-injecting electrode 4 and 11, respectively, which is of annular shape in the example shown. The current-injecting electrodes 4 and 11 are connected to the stimulating electrodes 1 and 2 by injection current generator 5 and 12, respectively.

The desired effect is achieved depending on the arrangement of the electrodes, on their geometry and on the forms of current chosen, for example a partial or even complete elimination of the current moving in the area of the subcutaneous receptors 7, a blockage of the nerve transmission between the receptors and the brain (anesthetizing effect), or an excitation of the area surrounding the receptors (TENS effect).

The undesirable sensations induced by a parasitic excitation of the subcutaneous receptors 7 are thus reduced, or masked, or even completely eliminated.

Figure 3:
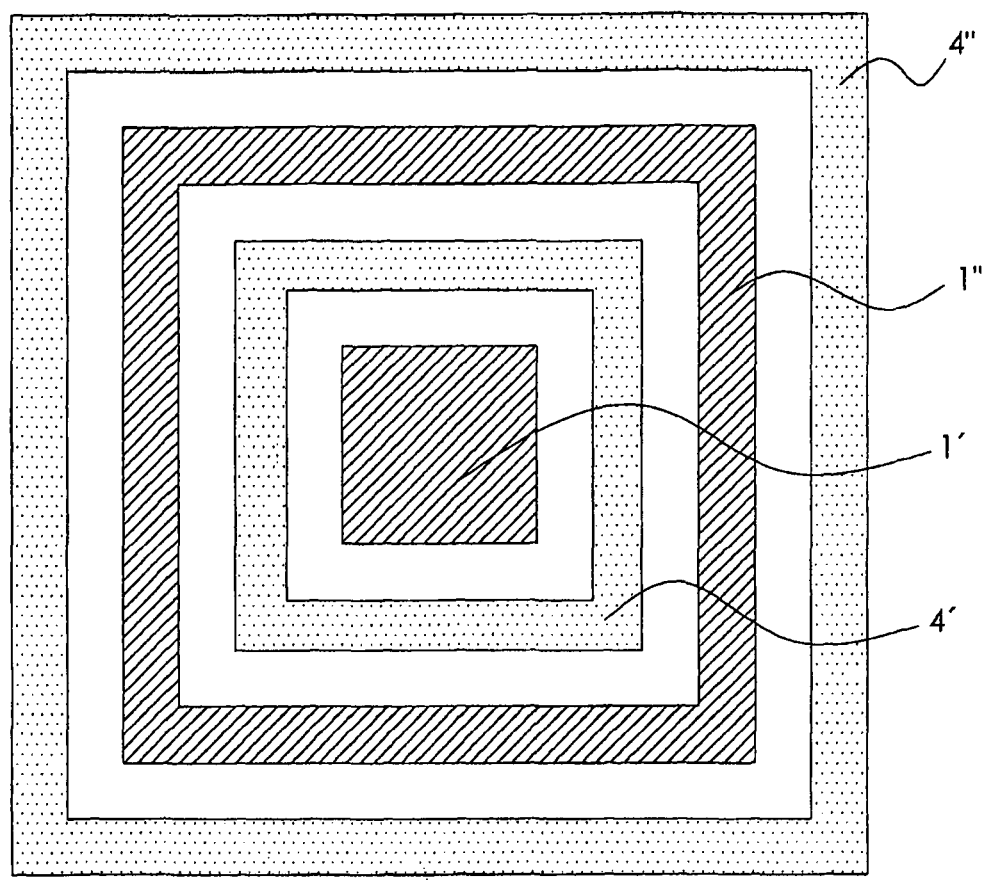
FIG. 3 illustrates another embodiment of the invention.

In the embodiment illustrated in FIG. 3, the stimulating electrode comprises a first part 1' surrounded by a first part of the current-injecting electrode 4', itself being surrounded by a second part of the stimulating electrode 1", which is itself surrounded by a second part of the current-injecting electrode 4". This configuration can of course repeat itself.

It goes without saying that the invention is not limited to the aforementioned examples.

Generally, it concerns any electrode configuration of the kind described above that makes it possible to reduce or eliminate the undesirable sensations resulting from an excitation of the subcutaneous receptors. In particular, the more one wishes the injection current to remain at the surface in the area of the subcutaneous receptors, the more the injecting and stimulating electrodes have to be placed near one another.

The invention claimed is:

1. An electrode system for transcutaneous nerve and/or muscle stimulation, comprising:
    a pair of stimulating electrodes, at least one of the pair of stimulating electrodes comprising a first part of the stimulating electrode and a second part of the stimulating electrode;
    a first current generator connected to the pair of stimulating electrodes, the first current generator configured to generate a nerve and/or muscle stimulation current between the pair of stimulating electrodes;
    a first current-injecting electrode comprising a first part and a second part, the first current-injecting electrode surrounding one of the pair of stimulating electrodes such that the first part and the second part of the first current-injecting electrode is disposed between the pair of stimulating electrodes when the pair of stimulating electrodes are positioned on a skin surface and;
    a second current generator connected to the first current-injecting electrode and at least one of the pair of stimulation electrodes, the second current generator configured to generate an injection current between the first current-injecting electrode and the connected at least one of the pair of stimulating electrodes for making subcutaneous receptors less excitable, wherein the first current-injecting electrode and the at least one of the pair stimulating electrodes are configured for placement on a skin surface such that the injection current does not extend depthwise but instead remains at the skin surface, the first part of the stimulating electrode is surrounded by the first part of the first current-injecting electrode, the first part of the first current-injecting electrode is surrounded by the second part of the stimulating electrode, and the second part of the stimulating electrode is surrounded by the second part of the first current-injecting electrode,
    wherein the pair of stimulating electrodes are separated by a distance, and wherein the first current-injecting electrode is arranged at a distance from one of the stimulating electrodes that is shorter than the distance between the pair of stimulating electrodes.

2. The electrode system of claim 1, further comprising a second current-injecting electrode.

3. The electrode system as claimed in claim 2, wherein each stimulating electrode is surrounded by a current-injecting electrode.

4. The electrode system as claimed in claim 2, wherein the first stimulating electrode comprises at least a first part surrounded by a first part of the first current-injecting electrode, the first part of the first current-injecting electrode is surrounded by a first part of the second stimulating electrode, and the first part of the second stimulating electrode is surrounded by a first part of the second current-injecting electrode.

5. The electrode system of claim 2, comprising:
- a second current generator that generates an injection current between a first of the pair of current-injecting electrodes and the first of the pair of stimulating electrodes; and
- a third current generator that generates an injection current between a second of the pair of current-injecting electrodes and the second of the pair of stimulating electrodes.

6. The electrode system of claim 1, wherein the first current-injecting electrode and the at least one of the stimulating electrodes are configured for placement on the skin surface such that the injection current does not extend depthwise but instead remains at the skin surface; wherein the second current generator is configured to deliver the injection current into an area of nearby subcutaneous receptors such that excitation of the subcutaneous receptors is reduced; and wherein the first current generator is configured to deliver the stimulation current to muscle or nerve tissue located beneath the subcutaneous receptors, whereby undesirable sensations resulting from excitation of the subcutaneous receptors by the stimulation current are reduced by the simultaneous delivery of the injection current.

7. A method of providing electrical stimulation, comprising the steps of:
- providing the electrode system of claim 1;
- placing the first current-injecting electrode and the at least one of the stimulating electrodes on a skin surface such that an injection current does not extend depthwise but instead remains at the skin surface;
- first generating the injection current by the second current generator and delivering the injection current into an area of nearby subcutaneous receptors such that excitation of the subcutaneous receptors is reduced; and then
- generating a stimulation current by the first current generator and delivering the stimulation current to muscle or nerve tissue located beneath the subcutaneous receptors,
- whereby undesirable sensations resulting from excitation of the subcutaneous receptors by the stimulation current are reduced by the simultaneous delivery of the injection current.

8. The method of claim 7,
wherein the injection current reduces a current density in the area of nearby subcutaneous receptors.

9. The method of claim 8, further comprising:
delivering the stimulation current from a first of the pair of stimulating electrodes into a second of the pair of stimulating electrodes; and
delivering the injection current from the current-injecting electrode into the first of the pair of stimulating electrodes.

10. The method of claim 8, further comprising:
delivering the stimulation current into a first of the pair of stimulating electrodes from a second of the pair of stimulating electrodes; and
delivering the injection current into the current-injecting electrode from the first of the pair of stimulating electrodes.

11. The method of claim 7, wherein the first current-injecting electrode and the stimulating electrodes are situated in a planar configuration on the skin surface.

12. A method for transcutaneous stimulation of a subject, comprising:
- generating a stimulation current between at least two stimulating electrodes;
- generating an injection current between a first of the at least two stimulating electrodes and a current-injecting electrode, wherein the first of the at least two stimulating electrodes comprises a first part and a second part, wherein the current-injecting electrode comprises a first part and a second part wherein the first part of the first of the at least two stimulating electrodes is surrounded b the first part of the current-injecting electrode wherein the first cart of the current-injecting electrode is surrounded by the second part of the first of the at least two stimulating electrodes, and wherein the second part of the first of the at least two stimulating electrodes is surrounded by the second part of the current injecting electrode, wherein the at least two stimulating electrodes have a distance therebetween, and wherein the current-injecting electrode is arranged at a distance from one of the at least two stimulating electrodes that is shorter than the distance between the at least two stimulating electrodes;
- delivering the stimulation current to nerve or muscle tissue located below the subject's skin surface and below the subject's subcutaneous receptors; and
- delivering the injection current to the subcutaneous receptors, but not to the nerve or muscle tissue, whereby undesirable sensations resulting from excitation of the subcutaneous receptors by the stimulation current are reduced by the simultaneous delivery of the injection current.

13. The method of claim 12, wherein the current-injecting electrodes and the stimulating electrodes are situated in a planar configuration on the skin surface.

14. A method of providing electrical stimulation, comprising the steps of:
- providing the electrode system of claim 5;
- placing the first of the pair of current-injecting electrodes and the first of the pair of stimulating electrodes on a skin surface such that an injection current does not extend depthwise but instead remains at the skin surface;
- generating, using the second current generator, the injection current between the first of the pair of current-injecting electrodes and the first of the pair of stimulating electrodes, wherein the injection current excites an area surrounding the subcutaneous receptors so as to induce a tingling sensation without inducing pain; and
- generating, using the third current generator, an injection current between a second of the pair of current-injecting electrodes and the second of the pair of stimulating electrodes, wherein the stimulation current is delivered to muscle or nerve tissue located beneath the subcutaneous receptors,
- whereby the tingling sensation resulting from delivery of the injection current masks pain caused by simultaneous delivery of the stimulation current.

* * * * *

UNITED STATES PATENT AND TRADEMARK OFFICE
CERTIFICATE OF CORRECTION

PATENT NO. : 9,008,791 B2  
APPLICATION NO. : 11/792635  
DATED : April 14, 2015  
INVENTOR(S) : Bühlmann et al.

Page 1 of 1

It is certified that error appears in the above-identified patent and that said Letters Patent is hereby corrected as shown below:

Column 4 line 31, Claim 1, change "surface and;" to --surface; and--.

Column 4 lines 33-34, Claim 1, change "stimulation" to --stimulating--.

Column 6 line 11, Claim 12, change "part" to --part,--.

Column 6 line 12, Claim 12, change "b" to --by--.

Column 6 line 13, Claim 13, change "electrode" to --electrode,--.

Column 6 line 14, Claim 12, change "cart" to --part--.

Signed and Sealed this  
Fifteenth Day of December, 2015

Michelle K. Lee  
*Director of the United States Patent and Trademark Office*